United States Patent [19]

Böger et al.

[11] 4,348,405
[45] Sep. 7, 1982

[54] PESTICIDAL SULFENYLS

[75] Inventors: Manfred Böger, Weil am Rhein, Fed. Rep. of Germany; Jozef Drabek, Oberwil, Switzerland

[73] Assignee: Ciba-Geigy Corporation, Ardsley, N.Y.

[21] Appl. No.: 293,805

[22] Filed: Aug. 17, 1981

[30] Foreign Application Priority Data

Aug. 26, 1980 [CH] Switzerland ................ 6419/80

[51] Int. Cl.³ .................. A01N 41/12; C07C 149/237
[52] U.S. Cl. ............................ 424/298; 260/453 RW
[58] Field of Search ................ 424/298; 260/453 RW

[56] References Cited

U.S. PATENT DOCUMENTS 3,847,951 11/1974 Kohn et al. .............. 260/346.2
3,897,463  6/1975 Kohn et al. .............. 260/346.2 R
4,179,514 12/1979 D'Silva ........................ 424/277

Primary Examiner—Dolph H. Torrence
Attorney, Agent, or Firm—Frederick H. Rabin

[57] ABSTRACT

The invention relates to N-sulfenyl-N-methylcarbamates and salts thereof with inorganic and organic acids of the formula

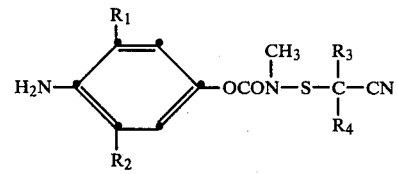

wherein $R_1$ is $C_1$–$C_4$ alkyl, $R_2$ is hydrogen or methyl, and each of $R_3$ and $R_4$ is methyl or, together with the carbon atom to which they are attached, both are a cyclopentyl radical.

A process for obtaining these compounds and their use in pest control are also described.

10 Claims, No Drawings

PESTICIDAL SULFENYLS

The present invention relates to N-sulfenyl-N-methylcarbamates and salts thereof with inorganic and organic acids, to the production of these compounds and to their use in pest control.

The N-sulfenyl-N-methylcarbamates of this invention have the formula

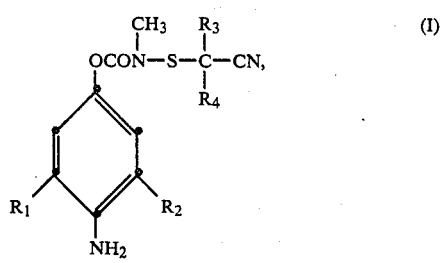

wherein $R_1$ is $C_1$–$C_4$ alkyl, $R_2$ is hydrogen or methyl, and each of $R_3$ and $R_4$ is methyl or, together with the carbon atom to which they are attached, both are a cyclopentyl radical.

Alkyl groups $R_1$ can be straight-chain or branched. Examples of such groups are: methyl, ethyl, propyl, isopropyl, and n-butyl, isobutyl, sec-butyl and tert-butyl.

Examples of suitable salt-forming inorganic acids are HCl, $H_2SO_4$, HBr and $H_3PO_4$, whilst suitable salt-forming organic acids are e.g. saturated and unsaturated monocarboxylic, dicarboxylic and tricarboxylic acids, for example formic acid, acetic acid, oxalic acid, phthalic acid and succinic acid.

The compounds of formula I can be obtained by methods which are known per se, e.g. as follows:

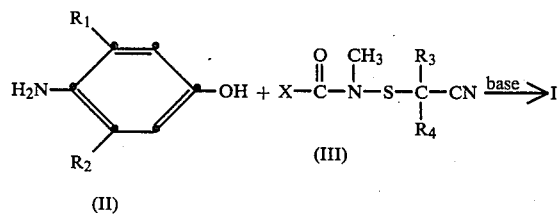

In formulae II and III above, $R_1$ to $R_4$ are as defined for formula I and X in formula III is a halogen atom, especially a fluorine or chlorine atom.

The process is carried out at a reaction temperature between $-50°$ and $+130°$ C., preferably between $-10°$ and $+100°$ C., under normal or slightly elevated pressure and in the presence of a solvent or diluent which is inert to the reactants.

Suitable bases for this process are, in particular, tertiary amines such as trialkylamines, pyridines and dialkyl anilines, and also hydroxides, oxides, carbonates and bicarbonates of alkali metals and alkaline earth metals, as well as alkali metal alcoholates, e.g. potassium tert-butylate and sodium methylate.

Examples of suitable solvents or diluents are: ethers and ethereal compounds such as diethyl ether, diisopropyl ether, dioxane, tetrahydrofurane; aliphatic and aromatic hydrocarbons, especially benzene, toluene, xylenes; and ketones such as acetone, methyl ethyl ketone and cyclohexanone.

The starting materials of the formulae II and III are known or they can be obtained by methods analogous to known ones.

The compounds of formula I are suitable for controlling pests of animals and plants. Hence these compounds have fungicidal and plant regulating properties. In particular, the compounds of formula I are suitable for controlling insects, phytopathogenic mites and ticks, e.g. of the order Lepidoptera, Coleoptera, Homoptera, Heteroptera, Diptera, Acarina, Thysanoptera, Orthoptera, Anoplura, Siphonaptera, Mallophaga, Thysanura, Isoptera, Psocoptera and Hymenoptera.

Most particularly, the compounds of formula I are suitable for controlling plant-destructive insects, especially plant-destructive feeding insects, in ornamentals and crops of useful plants, chiefly in cotton (e.g. against *Spodoptera littoralis* and *Heliothis virescens*) and in vegetables (e.g. against *Leptinotarsa decemlineata* and *Myzus persicae*).

In this connection, particular attention is drawn to the fact that the compounds of formula I have both a strongly pronounced systemic and also contact action against sucking insects, especially against sucking insects of the order Homoptera and, most particularly, against insects of the Aphididae family (e.g. against *Aphis fabae, Aphis craccivora* and *Myzus persicae*), which can only be controlled with difficulty using known pesticides.

The compounds of formula I also have a very useful action against flies, e.g. *Musca domestica*, and mosquito larvae. In addition, they have a broad ovicidal and ovilarvicidal action. Furthermore, the compounds of formula I have a useful action against phytoparasitic nematodes as well as against ectoparasitic mites and ticks, e.g. of the families Ixodidae, Argasidae and Dermanyssidae.

The compounds of the formula I are used in unmodified form or, preferably, together with the adjuvants conventionally employed in the art of formulation, and are therefore formulated in known manner to emulsifiable concentrates, suspension concentrates, directly sprayable or dilutable solutions, dilute emulsions, wettable powders, soluble powders, dusts, granulates, and also encapsulations in e.g. polymer substances. The methods of application, such as spraying, atomising, dusting, scattering or pouring, are chosen in accordance with the intended objectives and the prevailing circumstances, just like the nature of the compositions.

The formulations, i.e. the compositions or preparations containing the compound (active ingredient) of the formula I are prepared in known manner, e.g. by homogeneously mixing and/or grinding the active ingredients with extenders, e.g. solvents, solid carriers, and, where appropriate, surface-active compounds (surfactants).

Suitable solvents are: aromatic hydrocarbons, preferably the fractions containing 8 to 12 carbon atoms, e.g. xylene mixtures or substituted naphthalenes, aliphatic hydrocarbons such as cyclohexane, or paraffins, alcohols and glycols and their ethers and esters, ketones such as cyclohexanone, strongly polar solvents such as N-methyl-2-pyrrolidone, dimethyl sulfoxide or dimethyl formamide, as well as water.

The solid carriers used e.g. for dusts and dispersible powders, are normally natural mineral fillers, such as calcite, talcum, kaolinite, montmorillonite or attapulgite. In order to improve the physical properties it is also possible to add highly dispersed silicic acid or highly dispersed absorbent polymers. Suitable granulated absorptive carriers are porous types, for example pumice, broken brick, sepiolite and betonite; and suitable nonsorbent carriers are materials such as calcite or sand. In addition it is possible to use a great number of pregranulated materials of inorganic or organic nature, e.g. especially dolomite and extending to pulverised plant residues.

Depending on the polarity of the compound of the formula I to be formulated, suitable surface-active compounds are nonionic, cationic and/or anionic surfactants having good emulsifying, dispersing and wetting properties. The term "surfactants" will also be understood as comprising mixtures of surfactants.

Examples of suitable cationic surfactants are quaternary ammonium compounds such as cetyl trimethylammonium bromide. Examples of suitable anionic surfactants are soaps, salts of aliphatic monoesters of sulfuric acid or orthophosphoric acid, e.g. sodium laurylsulfate, salts of sulfonated aromatic compounds, e.g. sodium and calcium dodecylbenzenesulfonate, sodium, calcium and ammonium lignosulfonate, butylnaphthalenesulfonate, and a mixture of the sodium salts of diisopropyl- and triisopropylnaphthalenesulfonate as well as sodium diisobutylnaphthalenesulfonate. Examples of suitable non-ionic surfactants are the condensation products of ethylene oxide with fatty alcohols, e.g. oleyl alcohol or cetyl alcohol, or with alkyl phenols, e.g. octyl phenol, nonyl phenol and octyl cresol. Other non-ionic surfactants include partial esters which are derived from long-chain fatty acids and hexite anhydrides, and the condensation products of these partial esters with ethylene oxide, and lecithins.

The surfactants customarily employed in the art of formulation are described e.g. in "McCutcheon's Detergents and Emulsifiers Annual," MC Publishing Corp., Ringwood, New Jersey, 1979, and Sisely and Wood, "Encyclopedia of Surface Active Agents," Chemical Publishing Co. Inc., New York.

The pesticidal formulations usually contain 0.1 to 99%, preferably 0.1 to 95%, of a compound of the formula I, 1 to 99.9% of a solid or liquid adjuvant, and 0 to 25%, preferably 0.1 to 25%, of a surfactant.

Whereas commercial products are preferably formulated as concentrates, the end user will normally employ dilute formulations.

The formulations can also contain further additives such as stabilisers, antifoams, viscosity regulators, binders, adhesives, as well as fertilisers, in order to produce special effects.

Formulation Examples for liquid active ingredients of the formula I
(throughout, percentages are by weight)

| Emulsifiable concentrates | | |
|---|---|---|
| (a) | active ingredient | 20% |
| | calcium dodecylbenzenesulfonate | 5% |
| | castor oil polyethylene glycol ether (36 moles of ethylene oxide) | 5% |
| | xylene mixture | 70%; |
| (b) | active ingredient | 40% |
| | calcium dodecylbenzenesulfonate | 8% |
| | tributylphenol polyethylene glycol ether (30 moles of ethylene oxide) | 12% |
| | cyclohexanone | 15% |
| | xylene mixture | 25%; |
| (c) | active ingredient | 50% |
| | tributylphenol polyethylene glycol ether | 4.2% |
| | calcium dodecylbenzenesulfonate | 5.8% |
| | cyclohexanone | 20% |
| | xylene mixture | 20%. |

Emulsions of any required concentration can be produced from such concentrates by dilution with water.

| Solutions | | |
|---|---|---|
| (a) | active ingredient | 80% |
| | ethylene glycol monomethyl ether | 20%; |
| (b) | active ingredient | 10% |
| | polyethylene glycol 400 | 70% |
| | N-methyl-2-pyrrolidone | 20%; |
| (c) | active ingredient | 5% |
| | epoxidised vegetable oil | 1% |
| | petroleum fraction (boiling range 160°–190° C.) | 94%; |
| (d) | active ingredient | 95% |
| | epoxidised coconut oil | 5%. |

These solutions are suitable for application in the form of microdrops.

| Granulates | | |
|---|---|---|
| (a) | active ingredient | 5% |
| | kaolin | 94% |
| | highly dispersed silicic acid | 1%; |
| (b) | active ingredient | 10% |
| | attapulgite | 90%. |

The active ingredient is dissolved in methylene chloride, the solution is sprayed onto the carrier, and the solvent is subsequently evaporated off in vacuo.

| Dusts | | |
|---|---|---|
| (a) | active ingredient | 2% |
| | highly dispersed silicic acid | 1% |
| | talcum | 97%; |
| (b) | active ingredient | 5% |
| | highly dispersed silicic acid | 5% |
| | kaolin | 90%. |

Dusts which are ready for use are obtained by intimately mixing the carriers with the active ingredient.

Formulation examples for solid active ingredients of the formula I
(throughout, percentages are by weight)

| Wettable powders | | |
|---|---|---|
| (a) | active ingredient | 20% |
| | sodium lignosulfonate | 5% |
| | sodium laurylsulfate | 3% |
| | silicic acid | 5% |
| | kaolin | 67%; |
| (b) | active ingredient | 60% |
| | sodium lignosulfonate | 5% |
| | sodium diisobutylnapthalenesulfonate | 6% |
| | octylphenol polyethylene glycol ether (7–8 moles of ethylene oxide) | 2% |
| | highly dispersed silicic acid | 27%. |

The active ingredient is thoroughly mixed with the adjuvants and the mixture is thoroughly ground in a suitable mill, affording wettable powders which can be diluted with water to give suspensions of the desired concentration.

| Emulsifiable concentrate | |
| --- | --- |
| active ingredient | 10% |
| octylphenol polyethylene glycol ether (4-5 moles of ethylene oxide) | 3% |
| calcium dodecylbenzenesulfonate | 3% |
| castor oil polyglycol ether (36 moles of ethylene oxide) | 4% |
| cyclohexanone | 30% |
| xylene mixture | 50%. |

Emulsions of any required concentration can be obtained from this concentrate by dilution with water.

| Dusts | | |
| --- | --- | --- |
| (a) | active ingredient | 5% |
|  | talcum | 95%; |
| (b) | active ingredient | 8% |
|  | kaolin | 92%. |

Ready for use dusts are obtained by mixing the active ingredient with the carriers, and grinding the mixture in a suitable mill.

| Extruder granulate | |
| --- | --- |
| active ingredient | 10% |
| sodium lignosulfonate | 2% |
| carboxymethylcellulose | 1% |
| kaolin | 87%. |

The active ingredient is mixed and ground with the adjuvants, and the mixture is subsequently moistened with water. The mixture is extruded and then dried in a stream of air.

| Coated granulate | |
| --- | --- |
| active ingredient | 3% |
| polyethylene glycol 200 | 3% |
| kaolin | 94% |

The finely ground active ingredient is uniformly applied, in a mixer, to the kaolin moistened with polyethylene glycol. Non-dusty coated granulates are obtained in this manner.

| Suspension concentrate | |
| --- | --- |
| active ingredient | 40% |
| ethylene glycol | 10% |
| nonylphenol polyethylene glycol ether (15 moles of ethylene oxide) | 6% |
| sodium lignosulfonate | 10% |
| carboxymethylcellulose | 1% |
| 37% aqueous formaldehyde solution | 0.2% |
| silicone oil in the form of a 75% aqueous emulsion | 0.8% |
| water | 32%. |

The finely ground active ingredient is intimately mixed with the adjuvants, giving a suspension concentrate from which suspensions of any desired concentration can be obtained by dilution with water.

PREPARATORY EXAMPLES

EXAMPLE 1

(a) Preparation of (2-fluorocarbonyl-4-cyano-4-methyl)-2-aza-4-sulfapentane (starting material)

With stirring, 34.8 ml of methyl isocyanate are added at −50° C. to a solution of 11.7 g of anhydrous hydrofluoric acid in 100 ml of toluene. The reaction mixture is stirred for 2 hours and to the resultant solution are added 79.4 g of isobutyronitrilo-2-sulfenyl chloride, followed by the dropwise addition, with stirring, of 80.85 ml of triethylamine at −50° to −20° C. The reaction mixture is then stirred for 2 hours at −20° C., for 1 hour at room temperature, and finally for 1 hour at 50° C. The triethylamine hydrochloride formed is collected on a suction filter and the filtrate is concentrated by rotary evaporation. The crude product is distilled in a high vacuum, yielding the (2-fluorocarbonyl-4-cyano-4-methyl)-2-aza-4-sulfapentane of the formula

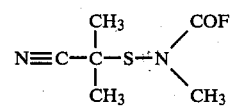

as a yellow liquid with a boiling point of 78°–80° C./0.25 mb.

(b) Preparation of N-(2-isobutyronitrilosulfenyl)-(3,5-dimethyl-4-aminophenyl)-N-methylcarbamate (final product)

To a solution of 6.85 g of 4-amino-3,5-dimethylphenol in 100 ml of methyl ethyl ketone are added 7 g of potassium carbonate. After stirring for 30 minutes at 20° C., 8.8 g of (2-fluorocarbonyl-4-cyano-4-methyl)-2-aza-4-sulfapentane are added slowly dropwise to the suspension. The reaction mixture is stirred for 8 hours at 60° C. bath temperature and then concentrated. The residue is taken up in methylene chloride and the organic phase is washed with water, dried and strongly concentrated. The residue is filtered over silica gel and the solution is concentrated, whereupon the product crystallises out.

Recrystallisation from toluene gives the compound of the formula

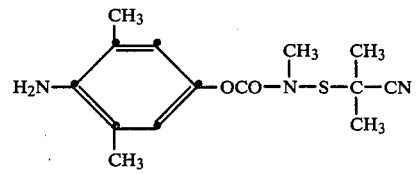

with a melting point of 119°–120° C.

The following compounds are prepared in analogous manner:

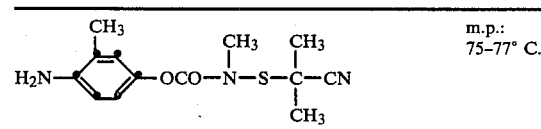

m.p.: 75–77° C.

-continued

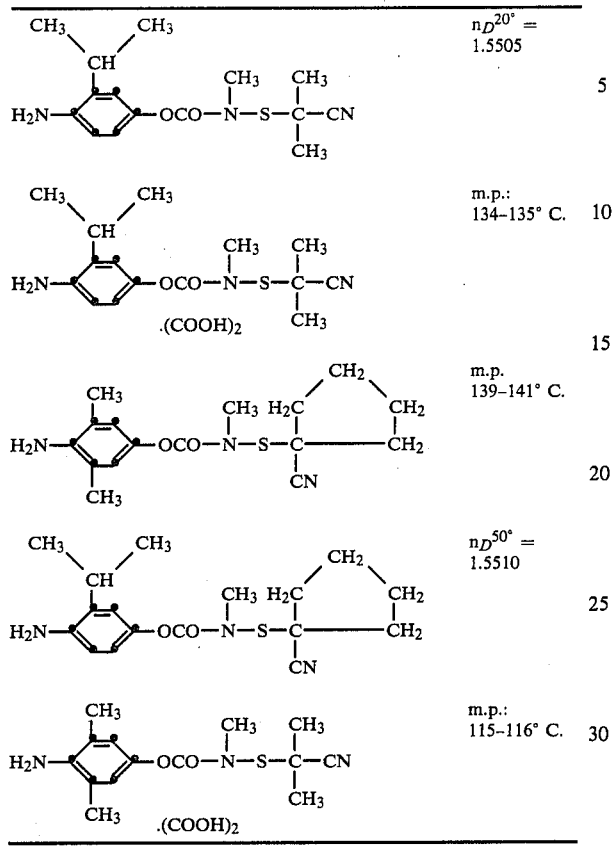

Biological Examples

EXAMPLE 2

Insecticidal stomach poison action against *Spodoptera littoralis, Dysdercus fasciatus* and *Heliothis virescens*

Cotton plants are sprayed with a solution containing 50, 100, 200 or 400 ppm of the compound to be tested. After the coating has dried, the plants are populated with larvae of the species *Spodoptera littoralis* (L3 stage), *Dysdercus fasciatus* (L4 stage) or *Heliothis virescens* (L3 stage). Two plants are used for each test compound and each test species. A mortality count is made after 2, 4, 24 and 48 hours. The test is carried out at 24° C. and 60% relative humidity.

Within the above indicated concentration limits, the compounds of Example 1 effect 100% kill of larvae of the species *Spodoptera littoralis, Dysdercus fasciatus* and *Heliothis virescens.*

EXAMPLE 3

Insecticidal contact action against *Myzus persicae*

Plants (Vicia faba) reared in water are each populated with about 200 insects of the species *Myzus persicae* before the start of the test. The treated plants are sprayed dripping wet from a distance of 30 cm 3 days later with a solution containing 10 or 1 ppm of the compound to be tested. Two plants are used for each test compound at its given concentration. A mortality count is made after a further 24 hours. Within the above indicated concentration limits, the compounds of Example 1 effect 100% kill of insects of the species *Myzus persicae.*

EXAMPLE 4

Systemic insecticidal action against *Aphis craccivora*

Bean plants which have grown roots are transplanted into pots containing 600 ccm of soil and then 50 ml of a solution containing 25 ppm, 5 ppm or 1 ppm of the compound to be tested are poured direct onto the soil.

After 24 hours the parts of the plants above the soil are populated with lice of the species *Aphis craccivora* and a plastic cylinder is then slipped over the plants to protect the lice from any possible contact with the test substance either directly or via the gas phase.

A mortality count is made 48 and 72 hours respectively after the start of the test. Two plants, each in a separate pot, are used for each test compound at its given concentration. The test is carried out at 25° C. and 70% relative humidity.

Within the above indicated concentration limits, the compounds of formula I effect 100% kill of insects of the species *Aphis craccivora.*

What is claimed is:

1. A N-sulfenyl-N-methylcarbamate, or a salt thereof with an inorganic or organic acid, of the formula

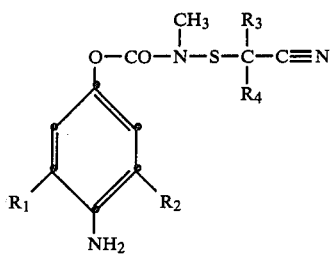

wherein $R_1$ is $C_1$–$C_4$ alkyl, $R_2$ is hydrogen or methyl, and each of $R_3$ and $R_4$ is methyl or, together with the carbon atom to which they are attached, both are a cyclopentyl radical.

2. The compound according to claim 1 of the formula

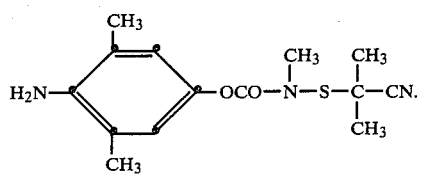

3. The compound according to claim 1 of the formula

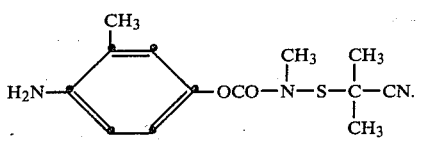

4. The compound according to claim 1 of the formula

5. The compound according to claim 1 of the formula

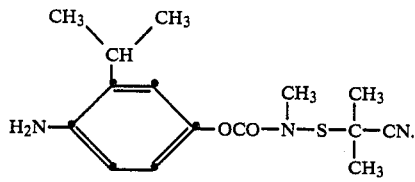

6. The compound according to claim 1 of the formula

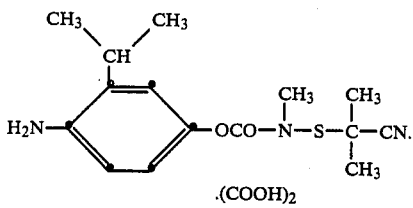

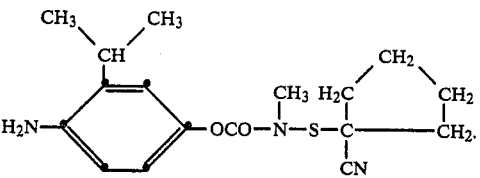

7. A process for the production of a compound according to claim 1, which process comprises reacting a compound of the formula

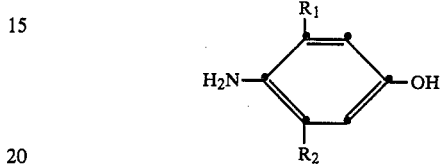

in the presence of a base, with a compound of the formula

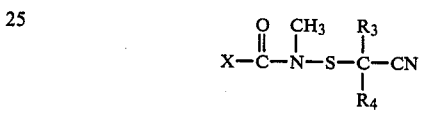

in which formulae $R_1$ to $R_4$ are as defined in claim 1 and X is a halogen atom.

8. A pesticidal composition which contains a compound according to claim 1 as active component.

9. A method of controlling pests of animals and plants at a locus, which comprises applying to said locus a compound according to claim 1.

10. A method according to claim 9, wherein the pests to be controlled are insects and representatives of the order Acarina.

* * * * *